(12) United States Patent
Teal et al.

(10) Patent No.: US 8,318,146 B1
(45) Date of Patent: Nov. 27, 2012

(54) ASCAROSIDES AS NEMATODE SEX PHEROMONES

(75) Inventors: Peter E. A. Teal, Gainesville, FL (US);
Hans T. Alborn, Gainesville, FL (US);
Paul W. Sternberg, Pasadena, CA (US);
Jagan Srinivasan, Pasadena, CA (US);
Arthur S. Edison, Gainesville, FL (US);
Fatma Kaplan, Gainesville, FL (US);
Frank C. Schroeder, Ithaca, NY (US)

(73) Assignees: The United States of America, as represented by the Secretary of Agriculture, Washington, DC (US); California Institute of Technology, Pasadena, CA (US)

( * ) Notice: Subject to any disclaimer, the term of this patent is extended or adjusted under 35 U.S.C. 154(b) by 633 days.

(21) Appl. No.: 12/362,850

(22) Filed: Jan. 30, 2009

Related U.S. Application Data (60) Provisional application No. 61/063,385, filed on Feb. 1, 2008.

(51) Int. Cl.
*A01N 43/16* (2006.01)
*C07H 15/00* (2006.01)
(52) U.S. Cl. .............................. 424/84; 514/25; 536/4.1
(58) Field of Classification Search .................. None
See application file for complete search history.

(56) References Cited

OTHER PUBLICATIONS

Simon et al., Evidence of a mate-finding cue in the hermaphrodite nematode *Caenorhabditis elegans*, PNAS (2002), vol. 99, No. 3, pp. 1598-1603.*
White et al., The Sensory Circuitry for Sexual Attraction in C. elegans Males, Current Biology (2007), doi:10.1016/j.cub.2007.09.011, pp. 1-11, S1-S7.*
Supplementary Figure 6 from Butcher et al., Small-molecule pheromones that control dauer development in *Caenorhabditis elegans*, Nature Chemical Biology (2007), vol. 3, No. 7, pp. 420-422 [online] [retrieved on Jan. 27, 2012]. Retrieved from the Internet <URL: http://www.nature.com/nchembio/journal/v3/n7/extref/nchembio. 2007.3-S6.pdf>.*
Srinivasan, Jagan, et al., "A blend of small molecules regulates both mating and development in *Caenorhabditis elegans*", Letters, Nature, vol. 454, Aug. 28, 2008, pp. 1115-1119.
Butcher, Rebecca A., et al, "Small-molecule pheromones that control dauer development in *Caenorhabditis elegans*", Letters, Nature Chemical Biology, No. 7, Jul. 2007, pp. 420-422.

* cited by examiner

*Primary Examiner* — Sue Liu
*Assistant Examiner* — Frank Choi
(74) *Attorney, Agent, or Firm* — John Fado; Albert Y. Tsui; Lesley Shaw

(57) ABSTRACT

A pheromonal compound produced by *Caenorhabditis elegans* has been identified as 5R-(3'-O-[β-D-glucosyl]-tetrahydro-3'R,5'R-dihydroxy-6'S-methyl-2H-pyran-2'R-yloxy)-2-hexanone. The novel compound, in combination with other ascarosides, elicit a synergistic signaling response from various adult male *Caenorhabditis* spp.

8 Claims, 11 Drawing Sheets

ASCR#1

ASCR#2

FIG. 1A

ASCR#3

ASCR#4

ASCAROSIDES AS NEMATODE SEX PHEROMONES

CROSS-REFERENCE TO RELATED APPLICATION

This present application claims priority under 35 U.S.C. §119(e) to U.S. Provisional Ser. No. 61/063,385, which was filed on Feb. 1, 2008, the disclosure of which is hereby incorporated by reference.

FIELD OF INVENTION

A pheromonal compound produced by *Caenorhabditis elegans* has been identified as 5R-(3'-O-[β-D-glucosyl]-tetrahydro-3'R,5'R-dihydroxy-6'S-methyl-2H-pyran-2'R-yloxy)-2-hexanone. The novel compound in combination with other ascarosides elicits a signaling response from a plurality of nematode species, namely *Caenorhabditis elegans*.

BACKGROUND OF INVENTION

In crops, root-knot nematodes are plant-parasitic nematode that damage a wide range of crops. Conversely, entomopathogenic nematodes are utilized as a biocontrol of soil insect pests. With respect to entomopathogenic nematodes, there has been an effort to isolate metabolites and to utilize isolated compounds as biopest control. For instance, U.S. Pat. No. 6,048,838 discloses a protein toxin isolated from *Xenorhabdus* strains as an insecticide.

The nematode *Caenorhabditis elegans*, population density is monitored via specific glycosides of the dideoxysugar ascarylose that promote entry into an alternate larval stage, the non-feeding and highly persistent dauer stage. While various ascarosides are known to induce dauer formation in *Caenorhabditis elegans*, (Butcher et al., 2007. *Nature Chemical Biology*, Vol. 3, Number 7:420:422) it remains to be determined whether there are other signal molecules beyond dauer formation. Specifically, a sex pheromone directed at male nematode attraction would be utilized to trap and reduce populations of plant-parasitic or animal-parasitic nematodes. Conversely, identification of a signaling pheromone would useful in attracting entomopathogenic nematodes to protect plants against insect pests. As such, there is need to determine whether a signaling attractant exists for nematodes.

BRIEF SUMMARY OF THE INVENTION

Disclosed is a novel ascaroside, 5R-(3'-O-[β-D-glucosyl]-tetrahydro-3'R,5'R-dihydroxy-6'S-methyl-2H-pyran-2'R-yloxy)-2-hexanone, that attracts adult male *Caenorhabditis elegans*. One aspect of the compound is that in combination with other ascarosides, the compound attracts adult male *Caenorhabditis elegans*. Disclosed is a method for attracting adult male nematodes to a locus comprising applying to said locus an effective amount of ascaroside. In an embodiment, the ascaroside attracts adult male *Caenorhabditis* spp. In an embodiment, the ascaroside is a combination of ascarosides selected from the group consisting of 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone. In another embodiment, the ascaroside is effective for attracting nematode selected from the group consisting of *Caenorhabditis elegans, Caenorhabditis brenneri, Caenorhabditis remanei, Caenorhabditis briggsae*, and *Caenorhabditis japonica*. In yet another embodiment, the effective amount of ascarosides are in an approximate ratio of 20 fmol:20 fmol:1 pmol for 5R-(Tetrahydro-3'R,5'R-dihydroxy-6'S-methyl-2H-pyran-2'R-yloxy)-2-hexanone: 8R-(Tetrahydro-3'R,5'R-dihydroxy-6'S-methyl-2H-pyran-2'R-yloxy)-2E-nonenoic acid: 5R-(3'-O-[β-D-glucosyl]-tetrahydro-3'R,5'R-dihydroxy-6'S-methyl-2H-pyran-2'R-yloxy)-2-hexanone. In still another embodiment, for attracting an adult male *Caenorhabditis* spp. to a locus comprising applying to said locus an effective amount of 8R-(Tetrahydro-3'R,5'R-dihydroxy-6'S-methyl-2H-pyran-2'R-yloxy)-2E-nonenoic acid in combination with a suitable carrier. In another embodiment, for attracting an adult male *Caenorhabditis* spp. to a locus comprising applying to said locus an effective amount of 5R-(Tetrahydro-3'R, 5'R-dihydroxy-6'S-methyl-2H-pyran-2'R-yloxy)-2-hexanone in combination with a suitable carrier. Also disclose is a synergistic nematode attractant composition comprising an effective amount of a synergistic combination of ascarosides, said ascarosides selected from the group consisting of 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone.

BRIEF DESCRIPTION OF THE DRAWING

The present invention together with the above and other objects and advantages may best be understood from the following detailed description of the embodiment of the invention illustrated in the drawings, wherein:

FIGS. 1A and 1B depict the chemical structures of various ascarosides. Specifically, FIG. 1A depicts the ascaroside: 6R-(Tetrahydro-3'R,5'R-dihydroxy-6'S-methyl-2H-pyran-2'R-yloxy)-heptanoic acid and 5R-(Tetrahydro-3'R,5'R-dihydroxy-6'S-methyl-2H-pyran-2'R-yloxy)-2-hexanone.

DETAILED DESCRIPTION OF THE INVENTION

Definitions

As used in the specification and claims, the singular form "a", "an" and "the" include plural references unless the context clearly dictates otherwise. For example, the term "a nematode" includes a plurality of nematodes.

The term "substantially pure chemical compound", as used in this specification and claims, refers to a chemical compound as a high degree of purity relative to the raw products from which the chemical compounds are derived. One of skill in the art will readily recognize that any chemical compound, even after purification, may contain a "contaminant" to a greater or lesser degree. Accordingly, although the purified chemical compounds have been "purified", absolute purity may not be necessarily be obtained, without significant sacrifice of yield. As used herein, the term "sex pheromone" or "attractant" refers to a chemical trigger that attracts members of the same species for the purposes of reproduction.

The term "effective amount" of a compound is an amount sufficient to induce a nematode specimen to change its behavior. An effective amount can be administered in one or more administrations. In terms of administering an "effective amount", such an amount sufficient to induce a nematode to a locus or to induce a nematode to increase its change of direction frequency would be an effective amount.

Figure 1A:
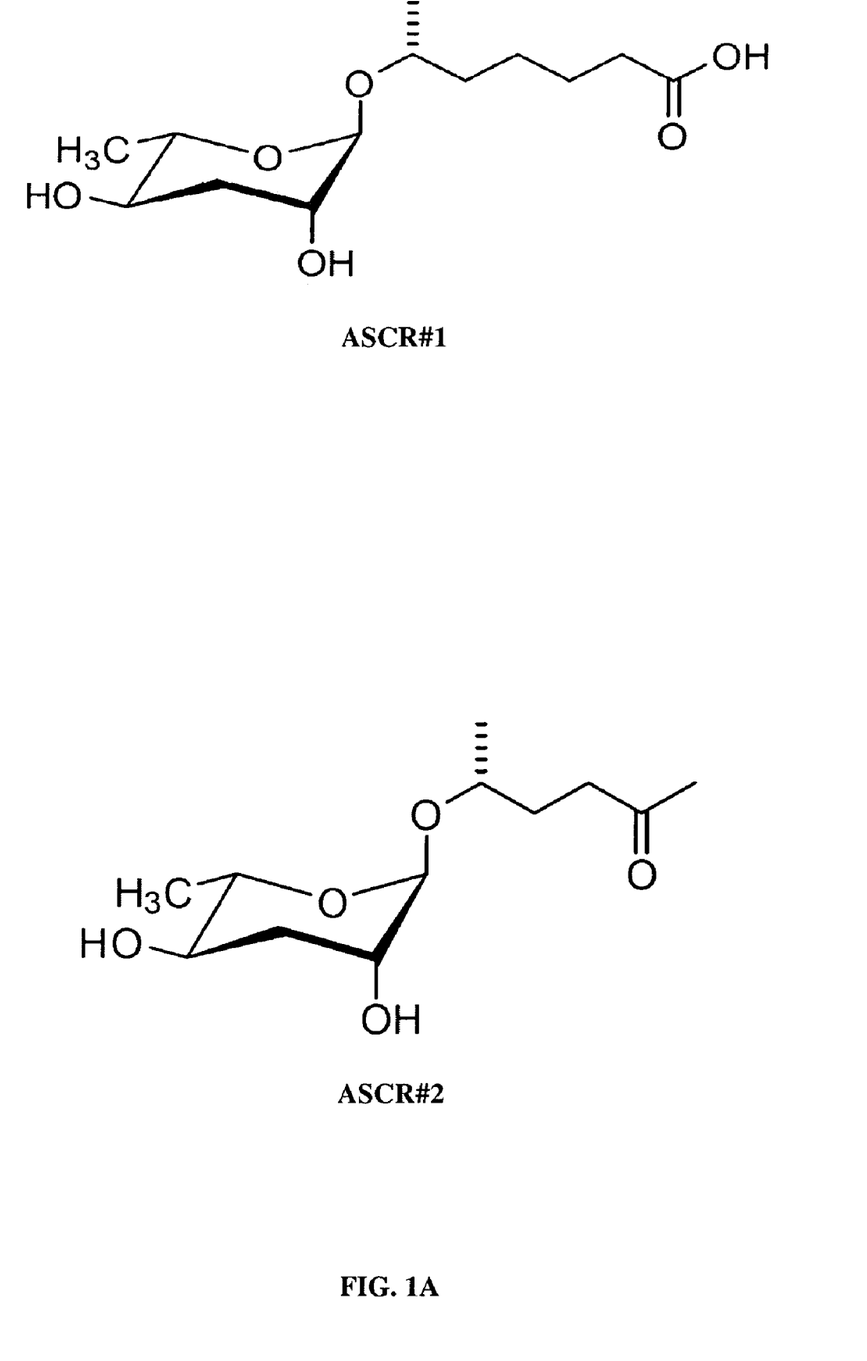
Figure 1B:
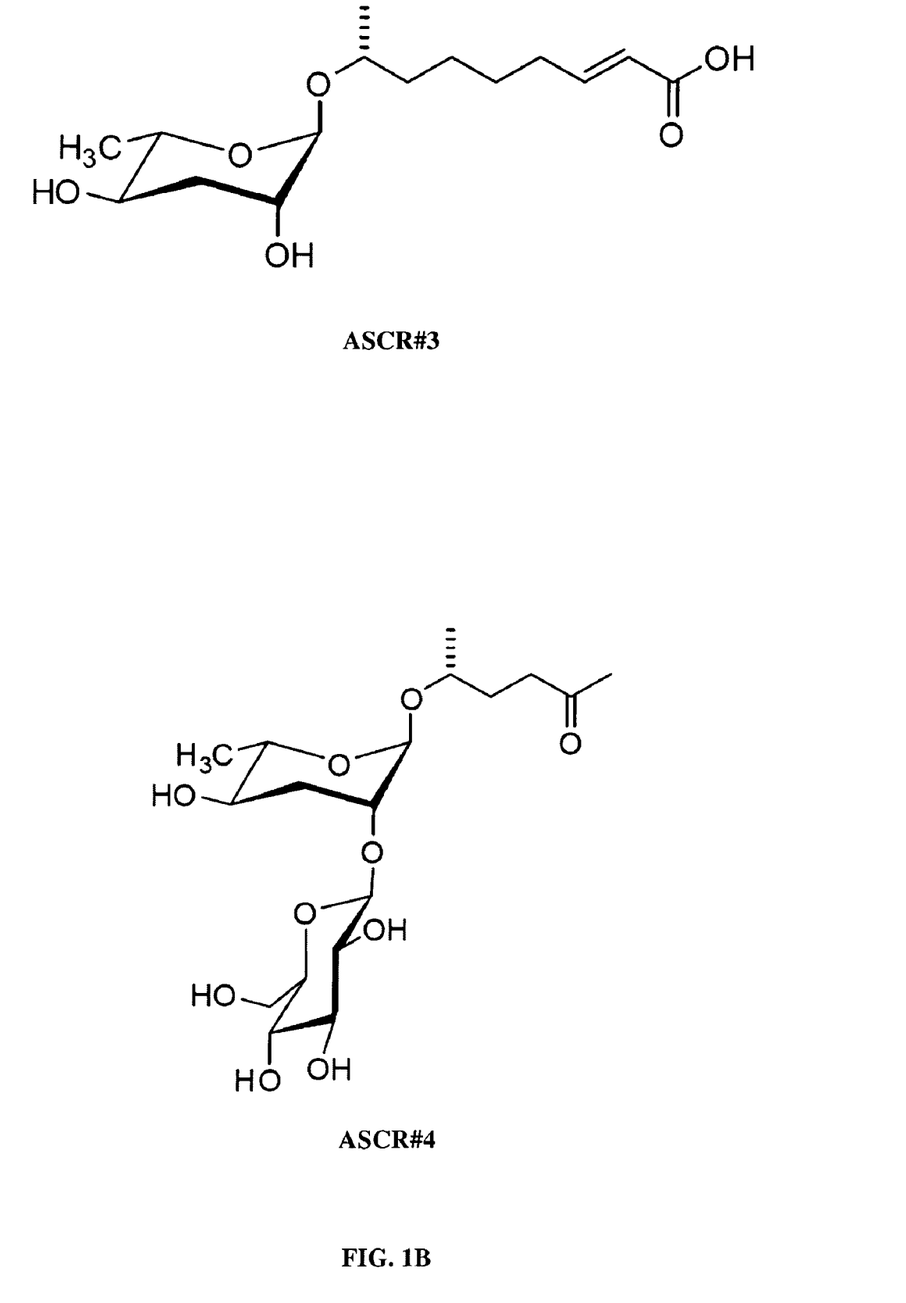
FIG. 1B depicts the ascaroside: 8R-(Tetrahydro-3'R,5'R-dihydroxy-6'S-methyl-2H-pyran-2'R-yloxy)-2E-nonenoic acid and the ascaroside: 5R-(3'-O-[β-D-glucosyl]-tetrahydro-3'R, 5'R-dihydroxy-6'S-methyl-2H-pyran-2'R-yloxy)-2-hexanone.

The term "ascaroside" as used in the specification and claims, refers to a group of glycolipids containing the sugar dideoxysugar ascarylose. Ascarosides include, but are not limited to 6R-(Tetrahydro-3R,5'R-dihydroxy-6'S-methyl-2H-pyran-2'R-yloxy)-heptanoic acid, 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone. As used in the specifications and the claims, 6R-(Tetrahydro-3'R,5'R-dihydroxy-6'S-methyl-2H-pyran-2'R-yloxy)-heptanoic acid and the molecular structure as depicted in FIG. 1A is also referred to as ASCR #1. As used herein, 5R-(Tetrahydro-3'R,5'R-dihydroxy-6'S-methyl-2H-pyran-2'R-yloxy)-2-hexanone and the molecular structure as depicted in FIG. 1A is also referred to as ASCR #2. As used herein, 8R-(Tetrahydro-3'R,5'R-dihydroxy-6'S-methyl-2H-pyran-2'R-yloxy)-2E-nonenoic acid and the molecular structure as depicted in FIG. 1B is also referred to as ASCR #3. As used herein, 5R-(3'-O-[β-D-glucosyl]-tetrahydro-3'R,5'R-dihydroxy-6'S-methyl-2H-pyran-2'R-yloxy)-2-hexanone and the molecular structure as depicted in FIG. 1B is also referred to as ASCR #4.

Nematode Strains and Media Extracts:

Wild-type *C. elegans* var. N2 Bristol and males from the CB1490 him-5(e1490) mutant were utilized in bioassays. The him-5(e1490) mutant segregates XO male progeny by X chromosome nondisjunction during meiosis. All strains were maintained at 20° C. unless detailed otherwise.

Other nematode strains used are AF16 *C. briggsae*, PB4641 *C. remanei*, DF5081 *C. japonica*, PB2801 *C. brenneri*, CU5248 (smIs26; him-5(e1490); ceh-30(tm272))$^2$, PS3981 osm-6(p811); him-8(e1489), PS299 osm-3(e1806); him-5(e1490), CB1489 him-8(e1489), DR476 daf-22 (m130). It is contemplated the ascarosides disclosed herein would act as sexual pheromones for adult nematodes.

Nematodes N2 were grown in liquid culture in 50 ml of S-media on a rotary shaker (220 rpm) for 10-12 days at 22° C., until a nematode density of about 4,000 nematodes per ml of media was reached. *E. coli* (OP50) was added as needed to the plate as a food source. Subsequently, the culture was centrifuged (140 g, 20 min) and the supernatant and nematode pellets were lyophilized separately. The dry residues representing supernatant and nematode pellet were powdered using a mortar and extracted separately with 95% ethanol at 20° C. for 16 hours. After filtration, the filtrates were evaporated to dryness and suspended in methanol. These mixtures were filtered again and the filtrates adjusted to a volume of 1 mL each.

*E. coli* (HB101) cultures were subjected to a mock treatment identical to the procedure described infra for the collection of *C. elegans* secreted metabolites. Similarly, *E. coli* (OP50) grown in LB broth at 37° C. were centrifuged, the bacterial pellet lyophilized, and subsequently extracted for the preparation of N2 media extracts. Both *E. coli* culture extracts were analyzed by LC-MS and NMR spectroscopy to confirm that they did not produce 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, or 5R-(3'-O-[β-D-glucosyl]- tetrahydro-3'R,5'R-dihydroxy-6'S-methyl-2H-pyran-2'R-yloxy)-2-hexanone. *E. coli* (HB101) was utilized a control specimen for liquid chromatography while *E. coli* (OP50) was utilized as the control for solid phase mating assays.

Caenorhabditis Mating Assay

Standard nematode growth medium plates (5 cm diameter) were used for assaying biological activity of the nematode conditioned water. The assay plates comprised of a thin lawn of an overnight grown *E. coli* OP50 culture with an approximate 0.25 cm gap between the bacterial lawn and the edge of the plate to prevent the nematodes from escaping. Plates were stored at room temperature (20° C.) for two days before being used in trials. Two spots (5 mm in diameter) were spotted 1.6 cm apart from each other on a template and stuck to the bottom of the assay plate. 0.8 µl of the control and the nematode metabolite were placed in the two circles and allowed to dry for approximately 30 seconds. To remove any bias, control and conditioned water spots were interchanged after every trial. Males and hermaphrodites were harvested daily at the fourth larval stage (L4) and stored at 20° C. overnight with 50-60 nematodes of the same sex per plate to be used as young adults the following day. Five nematodes were placed at approximately 1.0 cm away on each side (10 nematodes total) from the spots and allowed to acclimatize for 5 minutes. Trials were videotaped at 30 frames per second for 15 minutes using the Fire-i Unibrain software. For each sample, a minimum of 4-5 trials were conducted each day and each stage was tested on at least three different days.

Each time a nematode entered and left the scoring region it was scored as a nematode event. The time the nematode entered the scoring region and left the scoring region was recorded. Once inside the scoring region, the average time spent by each nematode was noted and the average time spent by the different nematode in the scoring region during the 15 minute interval (control and the conditioned water) were calculated.

Collecting *Caenorhabditis elegans* Secreted Metabolites:

Synchronized *C. elegans* (N2 Bristol) with a nematode density of 10,000 nematodes/ml was grown at 22° C. at 250 rpm on S-complete medium supplemented with *E. coli* (strain HB101): 1% for L2, 2% for L3, 3% for L4, 3% for YA, 4% for A, and 0% for L1 which was not fed. After nematodes reached the desired life stages, they were exposed to several wash and filtration (10 micron NITEX nylon filters) steps using M9 buffer to remove bacteria. The nematodes were collected between the washes either by a gentle centrifugation at 121 g for 30 s or by allowing the nematodes to settle for 10 min. To remove the bacteria in the gut of the nematodes, they were placed in M9 buffer in an incubator shaker for 30 min at 22° C. at 250 rpm, which was followed by three washes with ddH$_2$O, Subsequently *C. elegans* secreted metabolites were collected by incubating in ddH$_2$O in an incubator shaker for 1 h at 22° C. at 250 rpm with a nematode density of ~30,000 nematodes/ml for L2, L3, YA, A, ~15,000 nematodes/ml for L4, and ~100,000 nematodes/ml for L1. The nematodes were removed from conditioned water by a gentle centrifugation at 121 g for 10 s. The conditioned water was filtered through a 0.2 µm filter, lyophilized, and stored at −80° C.

Purification of Mate-Finding Pheromones:

Secreted metabolites were collected from 4 million YA nematodes using the method described supra. The purification involved a series of fractionation steps guided by the male attraction assay. Conditioned YA water was lyophilized and the residue suspended in H$_2$O. Reverse phase solid phase extraction was performed using Sep-Pak® Plus C18 cartridges (Waters, Mass.). The column was eluted sequentially with 50 and 90% MeOH. Strong adult male *Caenorhabditis elegan* attraction was observed for the active 50% MeOH fraction while hermaphrodites did not exhibit statistical significance (Unpaired t-test) for attraction to scoring region for the mating assay as described infra.

To further determine the active compounds in the fraction, the active 50% MeOH fraction was further fractionated by using an anion exchange column SAX (Alltech, Ill.) coupled to a cation exchange column SCX (Alltech, Ill.). After the neutral fraction was collected, the cation and anion columns were detached and eluted separately with 250, 500, and 1000 mM KCl. The 250, 500, and 1000 mM KCl fractions were desalted using C18 columns (Waters, Mass.).

Figure 2:
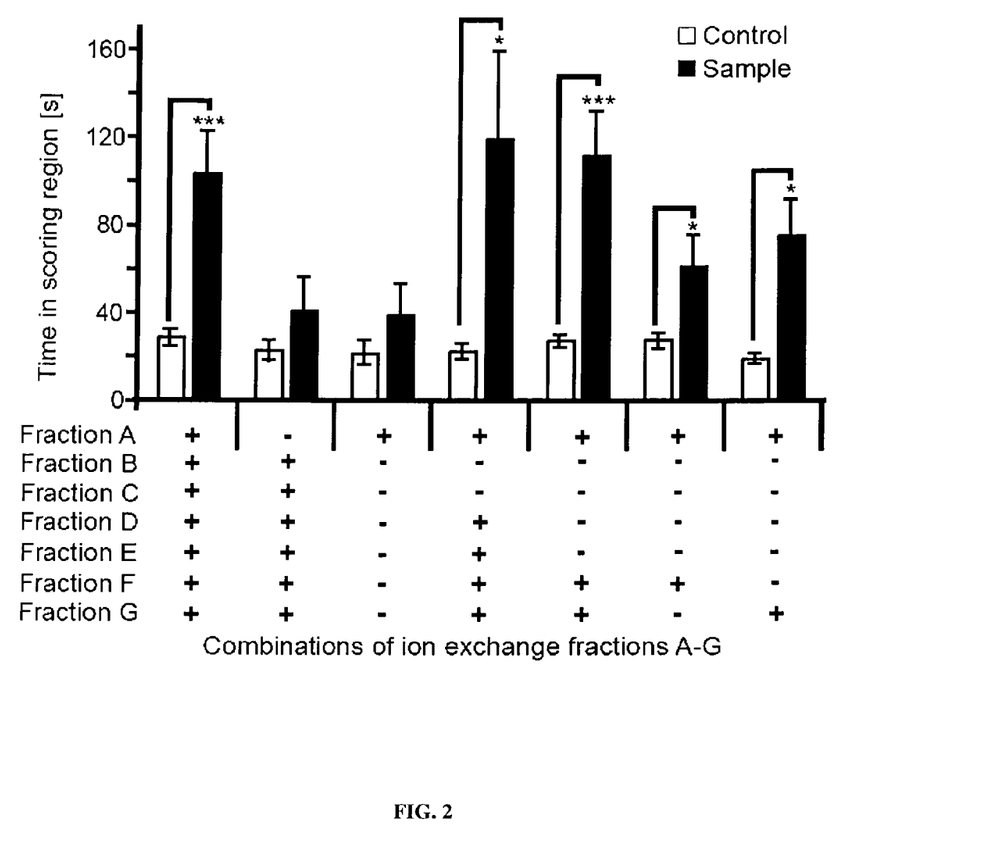
FIG. 2 depicts a graph of time spend by adult male *C. elegans* in a scoring region for mating bioassays as measured in seconds, with said scoring region marked with a combination of active fractions (fractions A-F). The mating assay was compared against $H_2O$ as a control.

Strong male attraction was observed for one of the resulting fractions, which was further fractionated using coupled ion-exchange columns. Of the resulting seven fractions A through G, none were active at physiologically relevant concentrations when tested individually, which suggested that male attraction depends on the synergy of two or more signaling molecules. To determine which fractions were required for activity, a series of combinations of fractions A-G were assayed; these assays showed that combination of fractions F or G with fraction A produced significant activity (FIG. 2).

The neutral fraction (Fraction A) was lyophilized and resuspended in 6 µl of D$_2$O containing 0.25 mM of the proton reference standard 3-(trimethylsilyl)propionic acid-D4 (TSP), for characterization via two-dimensional NMR spectroscopy including dqf-COSY, TOCSY, HSQC, HMBC, and NOESY. All NMR spectra were acquired at 27° C. using a 1-mm triple resonance high temperature superconducting (HTS) probe and a 600 MHz Bruker Avance II spectrometer. Total sample amount for these analyses corresponded to about 4 million W.E.

Ion-exchange fractions A, F, and G were analyzed further by liquid chromatography and mass spectrometry. A Thermo Finnigan LCQ Deca XP Max was used with electro spray ionization in positive or negative ion mode in the 50 to 1000 amu range (sheet gas 25 arb. units, sweep gas 5 arb. units, spray voltage 5.00 kV, capillary temperature 285° C. and capillary voltage 3.0 V.). Daughter ion spectra were obtained by a dependent scan of the most intense ion in a predefined mass range. The Thermo separations spectra HPLC system consisted of a quaternary pump P4000, autosampler AS 3000, diode array detector UV6000. The tertiary solvents are consisted of A: methanol with 0.05% formic acid, B: water with 10 mM ammonium formate and C: 90% acetonitrile/10% water with 10 mM ammonium formate. With the column temperature maintained at 60° C. and a solvent flow of 1.0 ml/min the C$_{18}$ column (ODS-AMQ, S-5 um, 200A, 250×4.6 mm I.D., YMC Co. Kyoto, Japan) eluted with a solvent composition starting with 4:90:6 (A:B:C) for two min followed by a gradient to 4:0:96 in 14 min and then kept at that composition for 5 min. UV absorption was monitored at 190 to 400 nm and the solvent flow between the UV detector and MS electro spray interface split 9:1 with a low volume micro needle valve splitter P450 (Upchurch Scientific) making it possible to obtain spectra of eluted compounds and simultaneously collect 90% of the injected material for bioassays.

Ascarosides 6R-(Tetrahydro-3'R,5'R-dihydroxy-6'S-methyl-2H-pyran-2'R-yloxy)-heptanoic acid, 5R-(Tetrahydro-3'R,5'R-dihydroxy-6'S-methyl-2H-pyran-2'R-yloxy)-2-hexanone, and 8R-(Tetrahydro-3'R,5'R-dihydroxy-6'S-methyl-2H-pyran-2'R-yloxy)-2E-nonenoic acid were synthesized from L-rhamnose and (2R)-propylene oxide (ASCR#1, ASCR#3)

or (2R,5R)-hexanediol (ASCR#2) as described in Butch et al., 2007. *Nature Chem. Biol.* 3, 420-422 and incorporated herein by reference.

5R-(3'-O-[β-D-glucosyl]-tetrahydro-3'R,5'R-dihydroxy-6'S-methyl-2H-pyran-2'R-yloxy)-2-hexanone was subsequently prepared from acetobromo-α-D-glucose and 5R-(Tetrahydro-3'R,5'R-dihydroxy-6'S-methyl-2H-pyran-2'R-yloxy)-2-hexanone. Specifically, silver carbonate (200 mg) was added to a stirred solution of 5R-(Tetrahydro-3'R,5'R-dihydroxy-6'S-methyl-2H-pyran-2'R-yloxy)-2-hexanone (7 mg, 0.03 mmol) in dichloromethane (2 ml) at 22° C. To the resulting suspension, a solution of acetobromoglucose (100 mg, 0.24 mmol) in 2 ml of dichloromethane was added over a period of 5 hours via syringe pump. After the addition was complete, stirring was continued for additional 2 hours. Subsequently, the mixture was filtered, the filter cake washed with ethyl acetate and the combined filtrates evaporated in vacuo. The resulting oil was dissolved in acetonitrile (0.5 ml) and purified via HPLC, using an Agilent (Santa Clara, Calif., USA) 1100 Series HPLC equipped with a quaternary pump, diode array detector, autosampler, and a reversed phase 25 cm×10 mm Supelco (Bellefonte, Pa., USA) Discovery HS C18 column. A solvent gradient was used, starting with 45% methanol in water for 3 min, followed by a linear increase of methanol content to 100% at 25 min, at a flow rate of 3.4 ml/min. Under these conditions, the tetraacetate of 5R-(3'-O-[β-D-glucosyl]-tetrahydro-3'R,5'R-dihydroxy-6'S-methyl-2H-pyran-2'R-yloxy)-2-hexanone eluted at 12.6 minutes, whereas its 4-glucosylated isomer eluted at 14.2 minutes. Fractions containing 5R-(3'-O-[β-D-glucosyl]-tetrahydro-3'R,5'R-dihydroxy-6'S-methyl-2H-pyran-2'R-yloxy)-2-hexanone from several HPLC runs were combined, and methanol and water were removed in vacuo, yielding 2 mg of the tetraacetate of 5R-(3'-[β-D-glucosyl]-tetrahydro-3'R,5'R-dihydroxy-6'S-methyl-2H-pyran-2'R-yloxy)-2-hexanone as a viscous oil. This material was re-dissolved in methanol and a solution of potassium carbonate (10 mg) in water (0.2 ml) was added. This mixture was stirred for 16 hours at 22° C. After evaporation of the methanol, the residue was diluted with water (0.3 ml) and purified using the aforementioned Agilent 1100 Series HPLC system and a solvent gradient starting with 5% methanol in water for 3 minutes, followed by a linear increase of methanol content reaching 100% at 25 minutes, at a flow rate of 3.4 ml/min. Under these conditions, ascr#4 eluted at 11.5 min. Fractions containing 5R-(3'-O-[β-D-glucosyl]-tetrahydro-3'R,5'R-dihydroxy-6'S-methyl-2H-pyran-2'R-yloxy)-2-hexanone from several HPLC runs were combined and evaporated in vacuo, yielding 1.2 mg of pure 5R-(3'-O[β-D-glucosyl]-tetrahydro-3'R,5'R-dihydroxy-6'S-methyl-2H-pyran-2'R-yloxy)-2-hexanone.

Stability of 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid Agar plates (total volume: 20 ml) prepared from Nobel agar and S-media containing ascr#2 and ascr#3 at a concentration of 200 nM were stored at room temperature for three months and subsequently lyophilized. The residue was powdered using a mortar and extracted with ethanol. The extract was evaporated to dryness, redissolved in 1 ml of methanol, and analyzed via LC-MS, using an Agilent 1100 HPLC system equipped with a 10×250 mm Supelco 5μ ODS preparative column eluted at a flow rate of 3.4 ml/min, and a Micromass Quattro II triple-quadrupole mass spectrometer operated in positive-electrospray ionization mode. A solvent gradient was used starting with a solvent composition of 5% methanol and 95% water, which was maintained for three minutes and then progressed linearly to 100% methanol by 40 minutes, resulting in retention times of 21.3 min (ascr#3) and 25.6 min (ascr#2). The LC-MS analyses revealed concentrations of 3.2 μM (ascr#3) and 3.5 μM (ascr#2) in the agar extract, corresponding to 80% (ascr#3) and 87% (ascr#2) recovery.

EXAMPLE 1

Identification of 5R-(3'-O-[β-D-glucosyl]-tetrahydro-3'R,5'R-dihydroxy-6'S-methyl-2H-pyran-2'R-yloxy)-2-hexanone Inasmuch as fraction A appeared to be required for full activity, the fraction was characterized using NMR spectroscopy and liquid chromatography-mass spectrometry (LC-MS) and detailed in Table 1).

TABLE 1

$^1$H and $^{13}$C NMR spectroscopic data for ascr#4 (600 MHz, D$_2$O).

| # | δH [ppm] | J [Hz] | δC [ppm] |
|---|---|---|---|
| 1 | 2.22 | | 31.74 |
| 2 | | | 218.90 |
| 3 | 2.70 | | 42.28 |
| 4a | 1.76 | | 32.89 |
| 4b | 1.82 | | |
| 5 | 3.86 | $J_{6,5} = 6.1$ | 74.31 |
| 6 | 1.17 | | 20.57 |
| 1' | 4.99 | $J_{1',2'} = 2, J_{1',3'b} = 1.5$ | 97.11 |
| 2' | 3.95 | $J_{2',3'a} = 3.0, J_{2',3'b} = 3.6$ | 78.80 |
| 3'a | 1.71 | $J_{3'a,3'b} = 13.9, J_{3'a,4'} = 11.3$ | 33.99 |
| 3'b | 2.21 | $J_{3'b,4'} = 4.4$ | 33.99 |
| 4' | 3.61 | $J_{4',5'} = 9.7$ | 69.44 |
| 5' | 3.66 | $J_{5',6'} = 6.1$ | 72.55 |
| 6' | 1.24 | | 19.29 |
| 1" | 4.57 | $J_{1",2"} = 7.9$ | 104.20 |
| 2" | 3.28 | $J_{2",3"} = 9.4$ | 75.59 |
| 3" | 3.48 | $J_{3",4"} = 9.3$ | 78.37 |
| 4" | 3.38 | $J_{4",5"} = 9.8$ | 72.30 |
| 5" | 3.44 | $J_{5",6"a} = 2.5, J_{5",6"b} = 5.9$ | 78.53 |
| 6"a | 3.88 | $J_{6"a,6"b} = 12.5$ | 63.34 |
| 6"b | 3.71 | | 63.34 |

Figure 8:
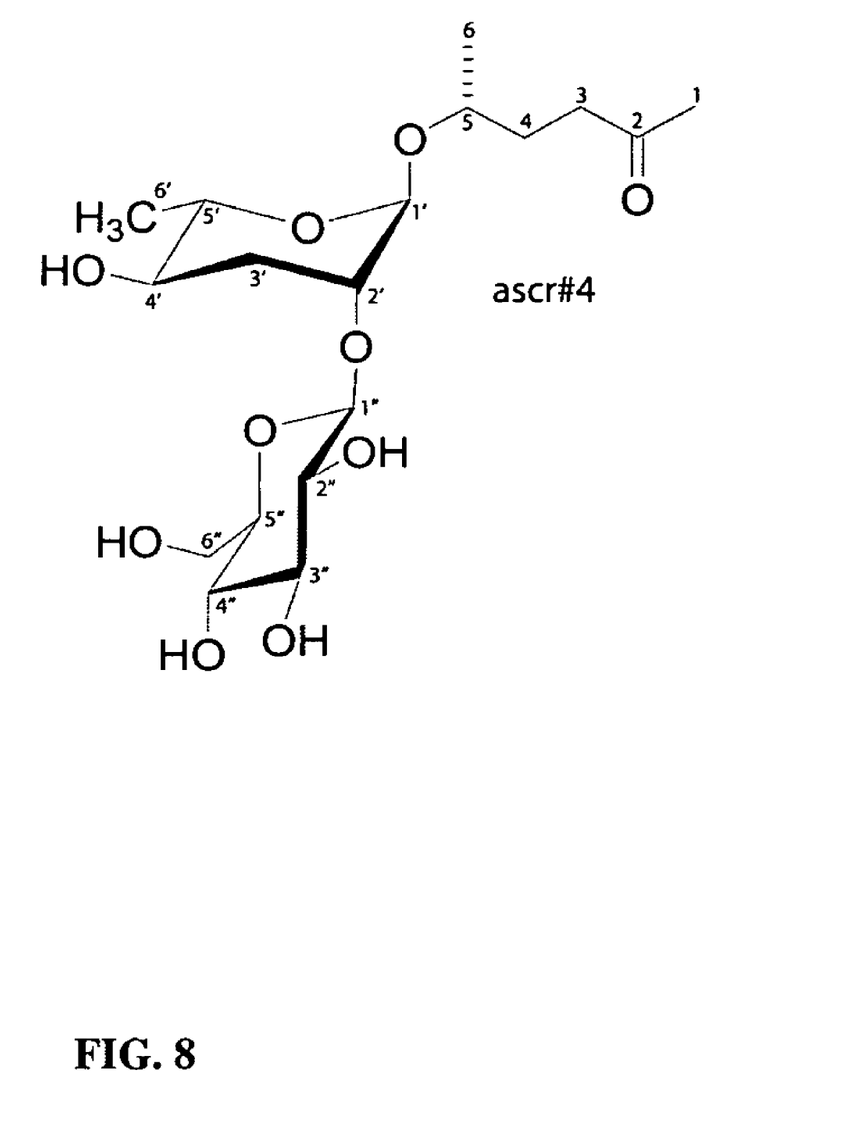
FIG. 8 disclosed the identity of compound in *Caenorhabditis elegans* metabolite fraction as determined by NMR spectroscopy.

Two-dimensional NMR spectroscopic analyses suggested that the major component in fraction A is a novel derivative of 5R-(Tetrahydro-3'R,5'R-dihydroxy-6'S-methyl-2H-pyran-2'R-yloxy)-2-hexanone "ASCR #2". Additional NMR-spectroscopic analyses showed that the major component of fraction A features a beta-glucosyl substituent attached to carbon #2 of the ascarylose in 5R-(Tetrahydro-3'R,5'R-dihydroxy-6'S-methyl-2H-pyran-2'R-yloxy)-2-hexanone. These assignments were corroborated by LC-MS analyses that showed m/z 426 representing the ammonium adduct (M+NH$_4^+$) of a compound with a nominal mass of 408 amu and molecular formula $C_{18}H_{32}O_{10}$. Comparison of these spectroscopic data with those of synthetic sample of 5R-(3'-O-[β-D-glucosyl]-tetrahydro-3'R,5'R-dihydroxy-6'S-methyl-2H-pyran-2'R-yloxy)-2-hexanone provided final proof for the identify of the major component of fraction A, which was identified as ASCR #4. See FIG. 8.

EXAMPLE 2

Attraction Synergism with Combination of 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid The identification of 5R-(3'-O-[β-D-glucosyl]-tetrahydro-3'R,5'R-dihydroxy-6'S-methyl-2H-pyran-2'R-yloxy)-2-hexanone in fraction A suggested that particular ascaroside plays a role as a mating signals. Therefore, the fractions required for activity, A, F, and G, was analyzed for the presence of additional ascarosides. Utilizing synthetic samples of ascarosides, 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid, male *Caenorhabdits elegans* were tested using the mating assay described supra. Consistent with the assay results for fractions A, F, and G, 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid were not active at physiological concentrations of 0 fmols to 10 fmol for 8R-(Tetrahydro-3'R,5'R-dihydroxy-6'S-methyl-2H-pyran-2'R-yloxy)-2E-nonenoic acid and 0 fmols to 100 fmols for 5R-(Tetrahydro-3'R,5'R-dihydroxy-6'S-methyl-2H-pyran-2'R-yloxy)-2-hexanone when each ascaroside was tested individually for the mating attraction assay. See FIG. 4.

However, at higher concentrations, 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid were both active. The corresponding dose-response curves show a strongly biphasic activity profile characteristic for many types of pheromones (See Carde et al., 1984. eds Hummel, H. E. & Miller, T. A., pgs 111-129 for pheromones having biphasic activity).

Figure 4:
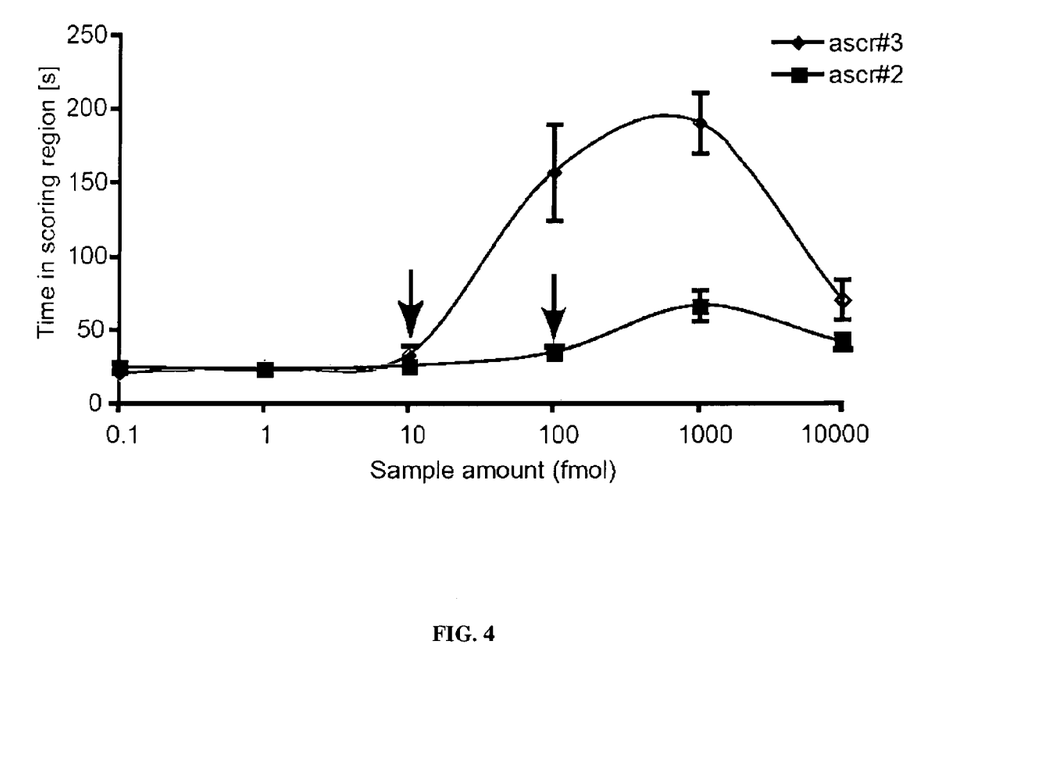
FIG. 4 depicts a graph of time spent by adult male *C. elegans* in a scoring region for a mating bioassay as measured in seconds, with said scoring region marked with the synthetic compounds 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid at a range of 0.1 fmol to 10,000 fmols.
Figure 5:
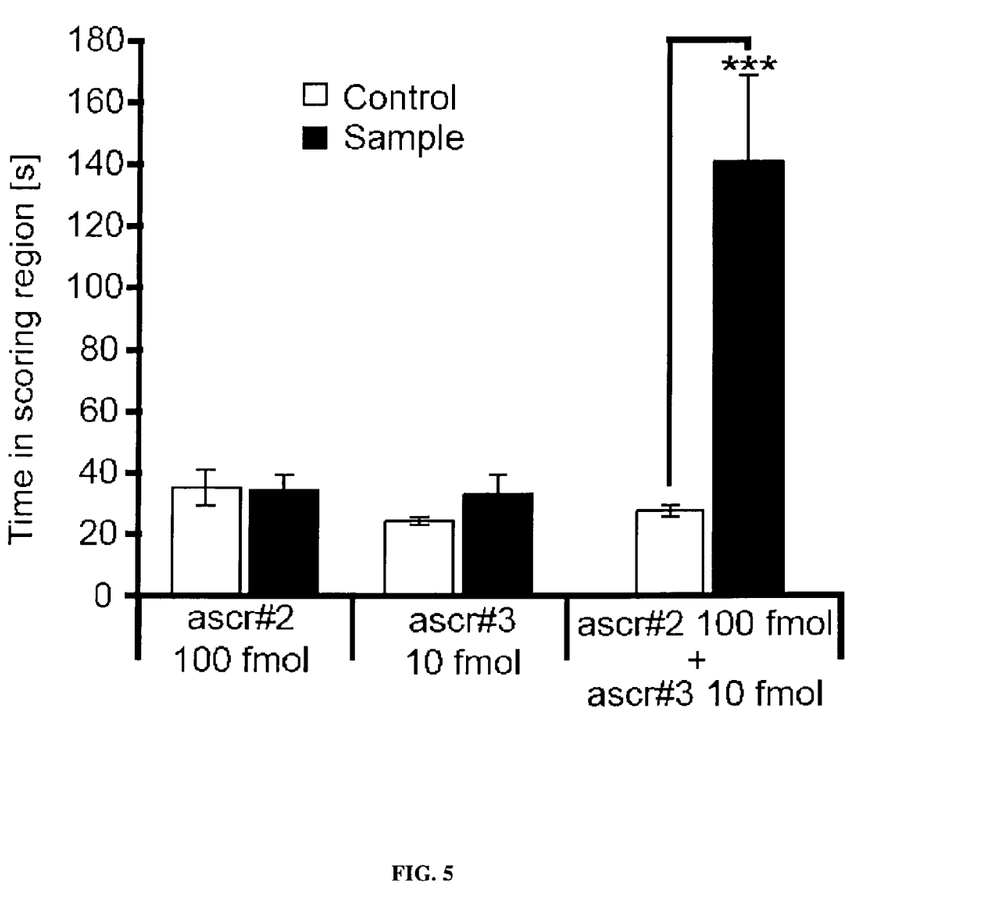
FIG. 5 depicts a graph of time spent by adult male *C. elegans* in a scoring region for a mating bioassay as measured in seconds, with said scoring region marked with the synthetic compounds 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid at 100 fmols and 10 fmols respectively. 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid were then combined to show a synergistic of time spent in the bioassay scoring region. The mating assay was compared against $H_2O$ as a control.

Because the assay results for the ion exchange fractions suggested that the mating signal consists of multiple compounds that act synergistically, a combination of 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid at concentrations that did not elicit significant male attraction when assayed individually (10 fmol ascr#3 and 100 fmol ascr#2, arrows in FIG. 4). The mixture produced a strong male attraction, demonstrating synergism of 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid (See FIG. 5).

EXAMPLE 3

Figure 3:
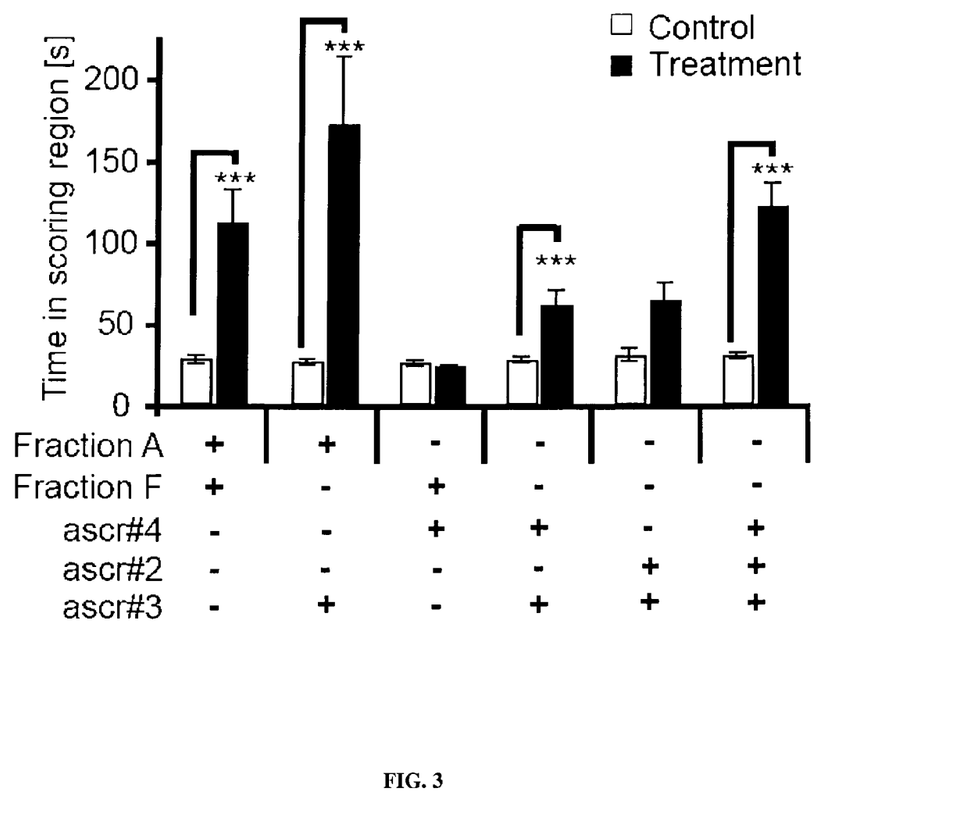
FIG. 3 depicts a graph of time spent by adult male *C. elegans* in a scoring region for mating bioassays as measured in seconds, with said scoring region marked with combinations of fractions A, F, synthetic compounds 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and/or 5R-(3'-O-[β-D-glucosyl]-tetrahydro-3'R,5'R-dihydroxy-6'S-methyl-2H-pyran-2'R-yloxy)-2-hexanone. The compounds are referenced as ASCR#2, ASCR#3, ASCR#4 and in molar concentrations of 1 pmol, 1 pmol, and 20 fmol respectively. The mating assay was compared against $H_2O$ as a control.

Attraction Synergism with Combination of 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone At the concentrations of 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid found in fractions A and F, a mixture of these two compounds also produced significant activity, but was less potent than the combination of fractions A and F (FIG. 3), suggesting synergy with a third component. Additional mating assays for adult male *Caenorhabdits elegans* using ternary mixtures of synthetic 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid and 5R-(3'-O-[β-D-glucosyl]-tetrahydro-3'R,5'R-dihydroxy-6'S-methyl-2H-pyran-2'R-yloxy)-2-hexanone were performed using the methods as detail supra. As detailed in FIG. 3, improved synergism for attraction was confirmed with the addition of 5R-(3'-O-[β-D-glucosyl]-tetrahydro-3'R,5'R-dihydroxy-6'S-methyl-2H-pyran-2'R-yloxy)-2-hexanone. The physiological mixture of 20 fmol of 5R-(Tetrahydro-3'R,5'R-dihydroxy-6'S-methyl-2H-pyran-2'R-yloxy)-2-hexanone, 20 fmol of 8R-(Tetrahydro-3'R,5'R-dihydroxy-6'S-methyl-2H-pyran-2'R-yloxy)-2E-nonenoic acid, and 1 pmol of 5R-(3'-O-[β-D-glucosyl]-tetrahydro-3'R,5'R-dihydroxy-6'S-methyl-2H-pyran-2'R-yloxy)-2-hexanone reproduced the activity in fractions A and F and elicited significantly stronger male attraction than a mixture of 20 fmol of 5R-(Tetrahydro-3'R,5'R-dihydroxy-6'S-methyl-2H-pyran-2'R-yloxy)-2-hexanone and 20 fmol 8R-(Tetrahydro-3'R,5'R-dihydroxy-6'S-methyl-2H-pyran-2'R-yloxy)-2E-nonenoic acid alone.

Figure 9:
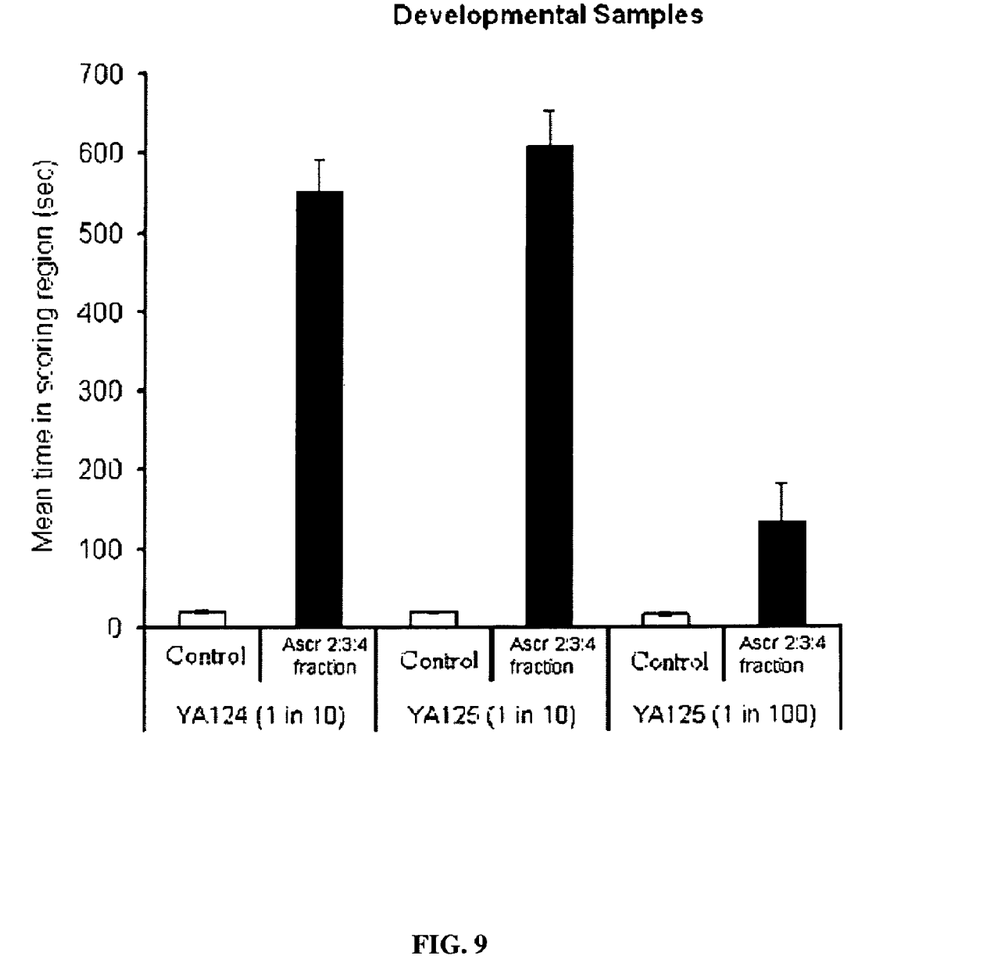
FIG. 9 depicts a graph of mean time spent by adult male *C. elegans* in a scoring region for a mating bioassay as measured in seconds marked with YA metabolite containing 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone.

Additionally, metabolites fractions collected YA *Caenorhabditis elegans* having acscaoside molar concentrations as detail in Table 2 infra. Ascaroside molar concentrations were calculated via liquid chromatography and mass spectrometry as detailed supra. As detailed in FIG. 9, YA secretions containing a combination of 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone at a molar concentration of approximately 0.5 pmols:0.055 pmols:0.789 pmols were subjected to mating bioassay respectively. Additionally, the secretions were diluted (1:100) and applied to mating assays.

TABLE 2

| | values for 1:10 dilution | | | values for 1:100 dilution | | |
|---|---|---|---|---|---|---|
| | ascr#4 pmol | ascr#3 pmol | ascr#2 pmol | ascr#4 pmol | ascr#3 pmol | ascr#2 pmol |
| YA124 | 0.789 | 0.055 | 0.537 | | | |
| YA125 | 0.757 | 0.054 | 0.618 | 0.076 | 0.005 | 0.062 |

EXAMPLE 4

Attraction Synergism with Various *Caenorhabditis* spp.

Figure 7:
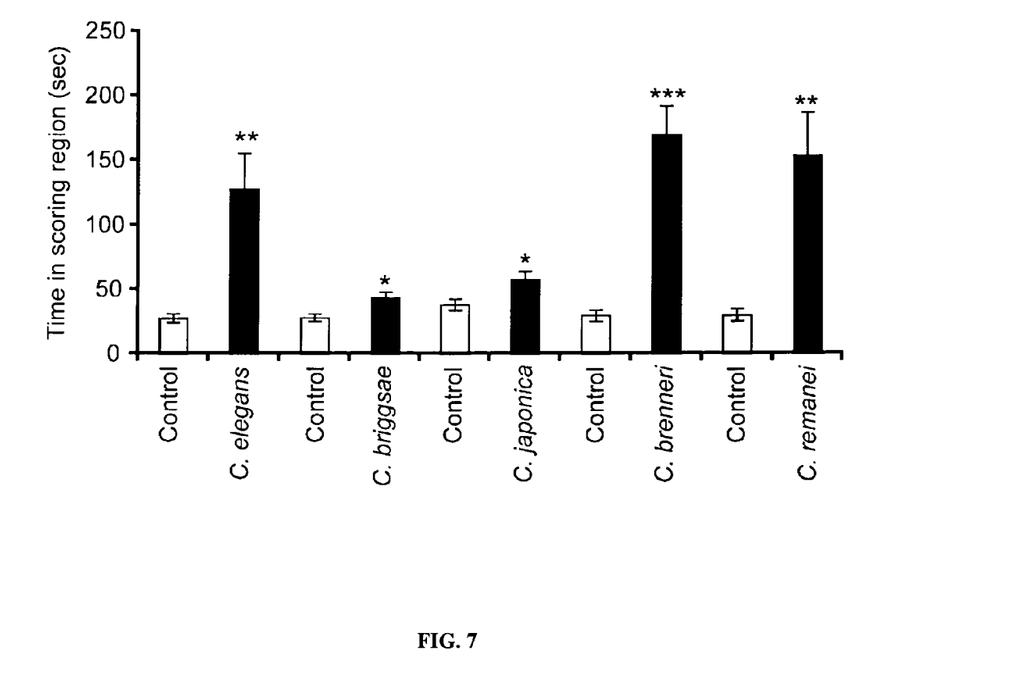
FIG. 7 depicts a graph of time spent by a plurality of adult male *Caenorhabditis* species in a scoring region for a mating bioassay as measured in seconds, with said scoring region marked with a ternary mix of synthetic compounds 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6'S-methyl-2H-pyran-2'R-yloxy)-2-hexanone at concentrations of 20 fmol, 20 pmol, and 1 fmol respectively.

A physiological mixture of 20 fmol of 5R-(Tetrahydro-3'R,5'R-dihydroxy-6'S-methyl-2H-pyran-2'R-yloxy)-2-hexanone, 20 fmol of 8R-(Tetrahydro-3'R,5'R-dihydroxy-6'S-methyl-2H-pyran-2'R-yloxy)-2E-nonenoic acid, and 1 pmol of 5R-(3'-O-[β-D-glucosyl]-tetrahydro-3'R,5'R-dihydroxy-6'S-methyl-2H-pyran-TR-yloxy)-2-hexanone was tested on a plurality of different species of the *Caenorhabditis* genus. *C. brenneri* and *C. remanei* males responded very similarly to the mixture as *C. elegans*, whereas, *C. briggsae* and *C. japonica* males responded only weakly (FIG. 7). It is contemplated that other nematodes as well as other *Caenorhabditis* spp. would be found attracted to the ascarosides and combination of ascarosides as disclosed herein. Additionally, it is contemplated that other nematode species having similar signal receptors would utilize be attached to the ascarosides and would have similar synergistic effects as disclosed herein.

EXAMPLE 5

Single Ascaroside Male Attraction Response

These results indicate that ascarosides regulate male attraction in *C. elegans*. To determine how these signaling molecules elicit such different biological responses, the activity profiles of single ascaroside for adult male *C. elegans* were determined using the mating assay as described supa. As detailed in FIG. 4, 8R-(Tetrahydro-3'R,5'R-dihydroxy-6'S-methyl-2H-pyran-2'R-yloxy)-2E-nonenoic acid elicited the strongest response for male attraction. Males spent approximately 6.6 fold more time in the 8R-(Tetrahydro-3'R,5'R-dihydroxy-6'S-methyl-2H-pyran-2'R-yloxy)-2E-nonenoic acid spotted region than in the control region, whereas 5R-(Tetrahydro-3'R,5'R-dihydroxy-6'S-methyl-2H-pyran-2'R-yloxy)-2-hexanone elicited a maximum ~2.8 fold increase. However, 5R-(3'-O-[β-D-glucosyl]-tetrahydro-3'R,5'R-dihydroxy-6'S-methyl-2H-pyran-2'R-yloxy)-2-hexanone and 6R-(Tetrahydro-3'R,5'R-dihydroxy-6'S-methyl-2H-pyran-2'R-yloxy)-heptanoic acid, were not active in the attraction assay at the 0 to 10000 fmol range of as tested.

EXAMPLE 6

Reversal Frequency

Given the nature of the attraction assay, the exact concentration of the compounds tested in the scoring region is not well defined. However, it seems likely that the test sample volume (1 µl) when added to the scoring region, is diluted by diffusion, suggesting that the actual concentrations of the assayed compounds on the plate were much lower than the original concentrations in the test sample volumes. Male *C. elegans* change direction of movement more frequently in the presence of an attractant which correlates with increase in time spent in the sample scoring region, suggesting that reversal frequency could be used as a measure for pheromone perception. Thus, an assay monitoring reversal frequency of males on agar plates with a range of concentrations of the most active pheromone components, 5R-(Tetrahydro-3'R,5'R-dihydroxy-6'S-methyl-2H-pyran-2'R-yloxy)-2-hexanone and 8R-(Tetrahydro-3'R,5'R-dihydroxy-6'S-methyl-2H-pyran-2'R-yloxy)-2E-nonenoic acid, using the automated nematode tracking system. A system used to track the sinusoidal movement of nematodes is disclosed in Cronin et al., 2005. *BMC Genet.* 6:5 and incorporated herein by reference.

For the tracker assays, standard nematode growth medium was prepared and added the different ascarosides to the required concentrations into the agar. Plates containing the ascarosides were then allowed to cool and stored at 20° C. overnight. Control plates were treated the same way except that instead of the ascaroside, an equivalent quantity of 100% ethanol was added to the agar. Assay plates were seeded with a thin lawn of an overnight grown *E. coli* OP50 culture and allowed to dry overnight. 10-15 L4 males were picked 14-16 hours before the experiment on *E. coli* OP50 seeded plates. For each assay, individual males were picked and placed on assay plates. After 5 minutes, males were assayed for 15 min using the automated tracker to get the different locomotion parameters. For each concentration of ascaroside, an equal number of males were tested on control plates. After the recordings, nematodes were processed using automated tracker software and the results were analyzed using in-house matlab scripts.

Figure 6A:
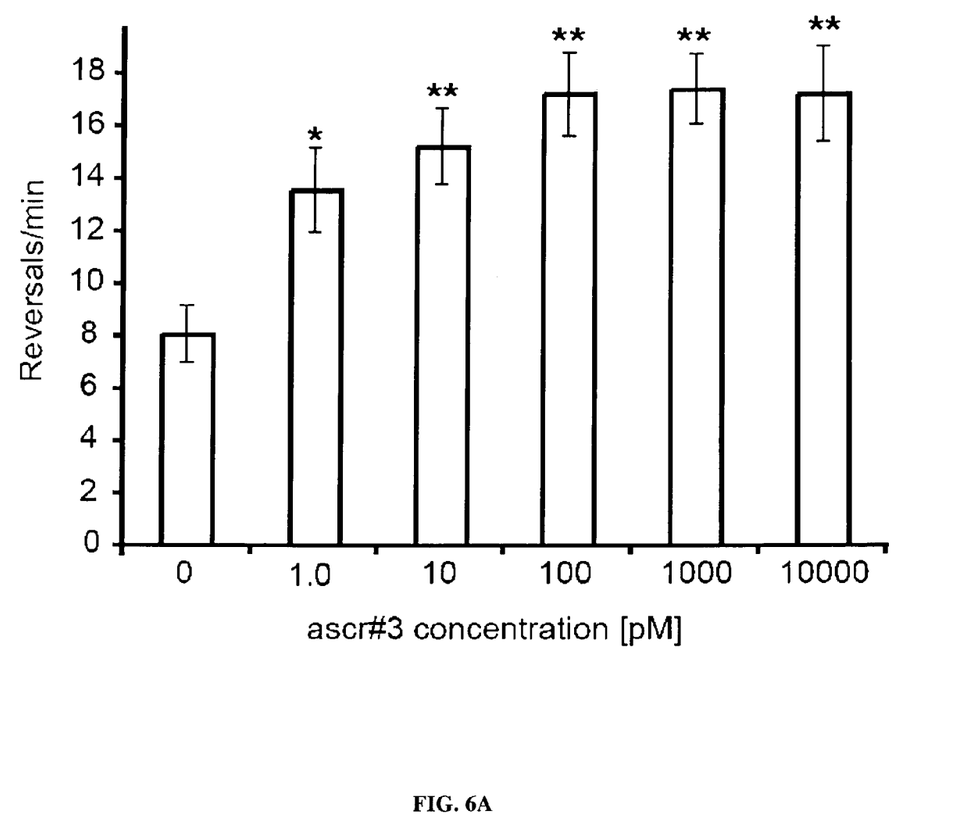
FIGS. 6A and 6B depict graphs of the reversal frequency of adult male *C. elegans* in upon exposure to 5R-(Tetrahydro-3'R,5'R-dihydroxy-6'S-methyl-2H-pyran-2'R-yloxy)-2-hexanone or 8R-(Tetrahydro-3'R,5'R-dihydroxy-6'S-methyl-2H-pyran-2'R-yloxy)-2E-nonenoic acid. For FIG. 6A, 8R-(Tetrahydro-3'R,5'R-dihydroxy-6'S-methyl-2H-pyran-2'R-yloxy)-2E-nonenoic acid was dosed at concentration range of 0 pmols to 10,000 pmols. For FIG. 6B, synthetic to 5R-(Tetrahydro-3'R,5'R-dihydroxy-6'S-methyl-2H-pyran-2'R-yloxy)-2-hexanone was dosed at a concentration range of 0 nmols to 100 nmols.
Figure 6B:
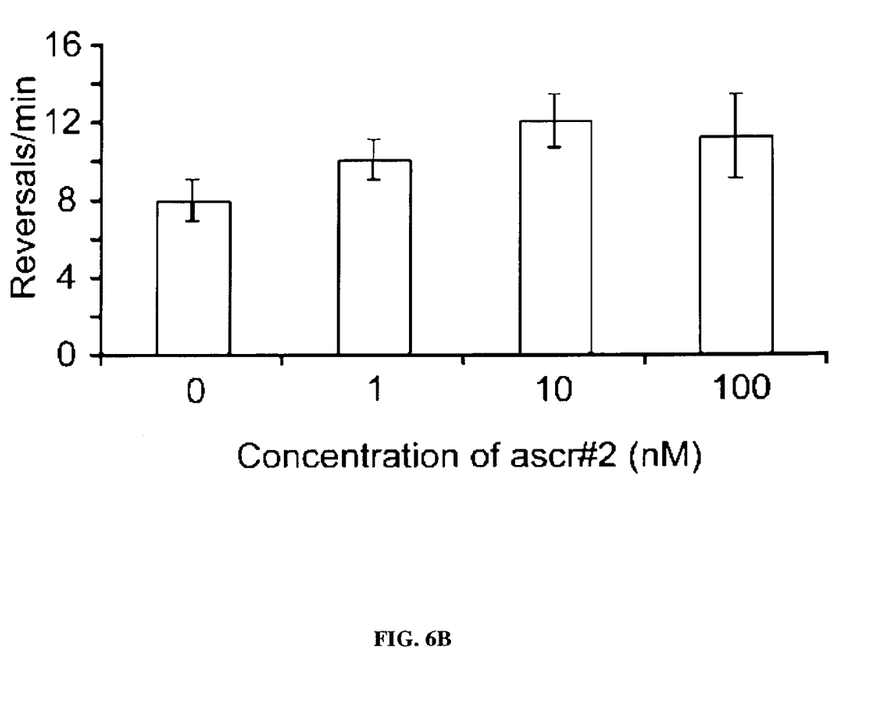

As shown in FIG. 6A, reversal frequency is increased by concentrations as low as 1 pM of 8R-(Tetrahydro-3'R,5'R-dihydroxy-6'S-methyl-2H-pyran-2'R-yloxy)-2E-nonenoic acid. For 5R-(Tetrahydro-3'R,5'R-dihydroxy-6'S-methyl-2H-pyran-2'R-yloxy)-2-hexanone, only weak increases of reversal frequency were observed. See FIG. 6B. These results suggest that ascr#3 acts as a male attractant at concentrations more than 10.000-fold lower than required for dauer induction.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. The compound 5R-(3'-O-[β-D-glucosyl]-tetrahydro-3'R,5'R-dihydroxy-6'S-methyl-2H-pyran-2'R-yloxy)-2-hexanone.

2. The compound of claim 1 wherein said compound is in combination with other ascarosides that attract adult male *Caenorhabditis elegans*.

3. A method for attracting adult male nematodes to a locus comprising applying to said locus an effective amount of a combination of ascarosides selected from the group consisting of 5R-(Tetrahydro-3'R,5'R-dihydroxy-6'S-methyl-2H-pyran-2'R-yloxy)-2-hexanone, 8R-(Tetrahydro-3'R,5'R-dihydroxy-6'S-methyl-2H-pyran-2'R-yloxy)-2E-nonenoic acid, and 5R-(3'-O-[β-D-glucosyl]-tetrahydro-3'R,5'R-dihydroxy-6S-methyl-2H-pyran-2'R-yloxy)-2-hexanone.

4. The method as described in claim 3 wherein said ascarosides are 5R-(Tetrahydro-3'R,5'R-dihydroxy-6'S-methyl-2H-pyran-2'R-yloxy)-2-hexanone: 8R-(Tetrahydro-3'R,5'R-dihydroxy-6'S-methyl-2H-pyran-2'R-yloxy)-2E-nonenoic acid: 5R-(3'-O-[β-D-glucosyl]-tetrahydro-3'R,5'R-dihydroxy-6'S-methyl-2H-pyran-2'R-yloxy)-2-hexanone and are in approximate molar ratio of 20 fmol:20 fmol:1 pmol.

5. The method as described in claim 3 wherein said nematode is a *Caenorhabditis* spp.

6. The method as described in claim 5 wherein said *Caenorhabditis* spp. is selected from the group consisting of *Caenorhabditis elegans, Caenorhabditis brenneri, Caenorhabditis remanei, Caenorhabditis briggsae,* and *Caenorhabditis japonica*.

7. A method of attracting an adult male *Caenorhabditis* spp. to a locus comprising applying to said locus an effective amount of 8R-(Tetrahydro-3'R,5'R-dihydroxy-6'S-methyl-2H-pyran-2'R-yloxy)-2E-nonenoic acid in combination with a suitable carrier.

8. A method of attracting an adult male *Caenorhabditis* spp. to a locus comprising applying to said locus an effective amount of 5R-(Tetrahydro-3'R,5'R-dihydroxy-6'S-methyl-2H-pyran-2'R-yloxy)-2-hexanone in combination with a suitable carrier.

* * * * *